(12) United States Patent
Suzuki et al.

(10) Patent No.: US 12,326,429 B2
(45) Date of Patent: Jun. 10, 2025

(54) GAS MEASUREMENT DEVICE AND GAS MEASUREMENT METHOD

(71) Applicants: SINTOKOGIO, LTD., Nagoya (JP); National University Corporation TOYOHASHI UNIVERSITY OF TECHNOLOGY, Toyohashi (JP)

(72) Inventors: Yoshihisa Suzuki, Toyokawa (JP); Toshihiko Noda, Toyohashi (JP); Kazuaki Sawada, Toyohashi (JP)

(73) Assignees: SINTOKOGIO, LTD., Nagoya (JP); National University Corporation TOYOHASHI UNIVERSITY OF TECHNOLOGY, Toyohashi (JP)

( * ) Notice: Subject to any disclaimer, the term of this patent is extended or adjusted under 35 U.S.C. 154(b) by 211 days.

(21) Appl. No.: 17/802,269

(22) PCT Filed: Feb. 3, 2021

(86) PCT No.: PCT/JP2021/003924
§ 371 (c)(1),
(2) Date: Aug. 25, 2022

(87) PCT Pub. No.: WO2021/176933
PCT Pub. Date: Sep. 10, 2021

(65) Prior Publication Data
US 2023/0079310 A1   Mar. 16, 2023

(30) Foreign Application Priority Data
Mar. 5, 2020   (JP) ................... 2020-038064

(51) Int. Cl.
*G01N 27/00* (2006.01)
*G01N 33/00* (2006.01)

(52) U.S. Cl.
CPC ..... *G01N 33/0013* (2013.01); *G01N 33/0073* (2013.01)

(58) Field of Classification Search
CPC .................................................. G01N 33/0013
See application file for complete search history.

(56) References Cited

U.S. PATENT DOCUMENTS

| 4,840,913 A | 6/1989 | Logothetis et al. |
| 5,705,129 A | 1/1998 | Takahashi et al. |

(Continued)

FOREIGN PATENT DOCUMENTS

| DE | 199 16 798 A1 | 11/2000 |
| JP | H8-278272 A | 10/1996 |

(Continued)

OTHER PUBLICATIONS

Extended Eurpoean Search Report issued Jan. 29, 2024 in Application No. 21764007.7.

(Continued)

*Primary Examiner* — Herbert K Roberts
(74) *Attorney, Agent, or Firm* — Faegre Drinker Biddle & Reath LLP

(57) ABSTRACT

The gas measurement device includes a catalyst member connected to a power source applying voltage or current, performing a reaction of a first gas and a second gas contained in a mixed gas contacted with the catalyst member to generate a third gas, and exhibiting a catalytic action in which the reaction changes in response to temperature, and a gas sensor configured to detect gas molecules contacted with the catalyst member.

16 Claims, 5 Drawing Sheets

(56) References Cited

U.S. PATENT DOCUMENTS

| | | | | |
|---|---|---|---|---|
| 6,187,597 B1 | * | 2/2001 | Lundstrom | ........ G01N 33/0031 |
| | | | | 436/152 |
| 2010/0106039 A1 | | 4/2010 | Abraham-Fuchs et al. | |
| 2017/0065208 A1 | | 3/2017 | Furusaki et al. | |
| 2023/0314354 A1 | * | 10/2023 | Mizutani | ............ G01N 33/0013 |
| | | | | 73/23.31 |

FOREIGN PATENT DOCUMENTS

| | | | | |
|---|---|---|---|---|
| JP | H11-281612 A | | 10/1999 | |
| JP | 2002-096050 A | | 4/2002 | |
| JP | 2018179842 A | * | 11/2018 | |
| JP | 2020-076690 A | | 5/2020 | |
| WO | WO-97/005476 A1 | | 2/1997 | |
| WO | WO-2015091234 A1 | * | 6/2015 | ......... G01N 21/1702 |
| WO | WO-2017/082431 A1 | | 5/2017 | |

OTHER PUBLICATIONS

International Preliminary Report on Patentability mailed Sep. 15, 2022 for PCT/JP2021/003924.
Office Action mailed Apr. 3, 2025 for counterpart EP Patent Application No. 21764007.7.

* cited by examiner

Fig.2
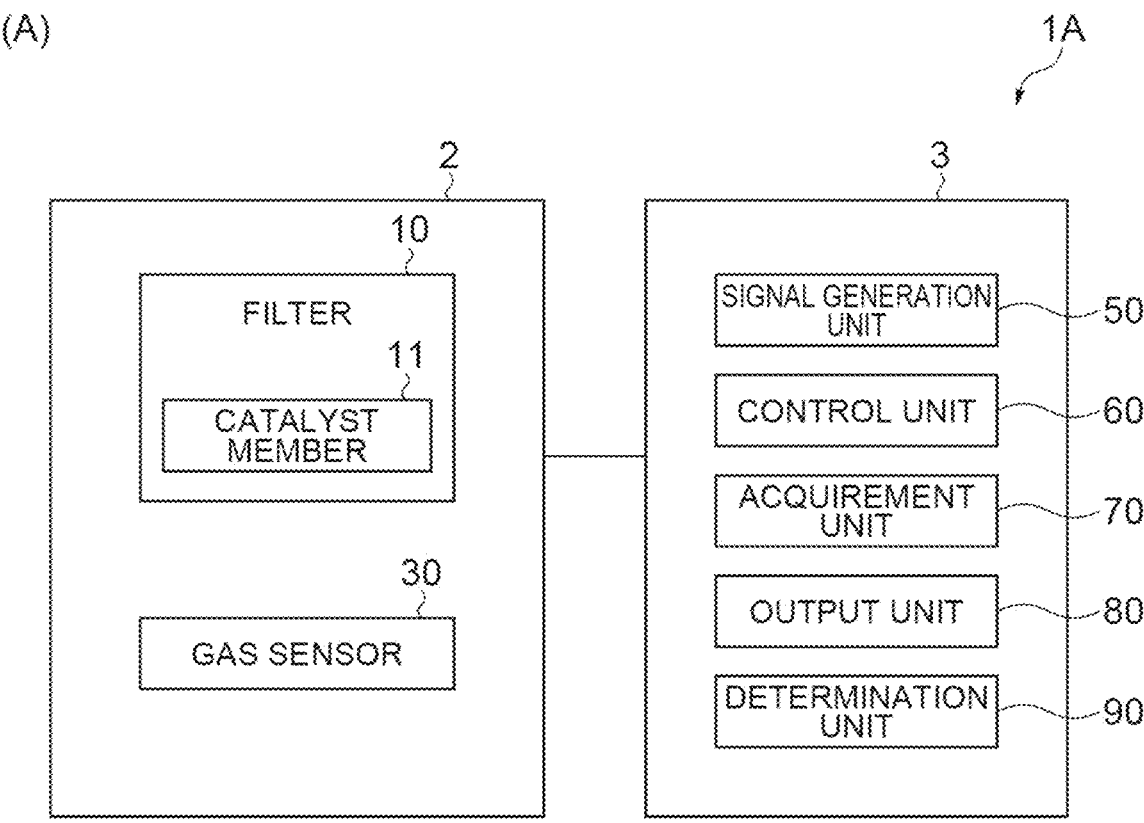
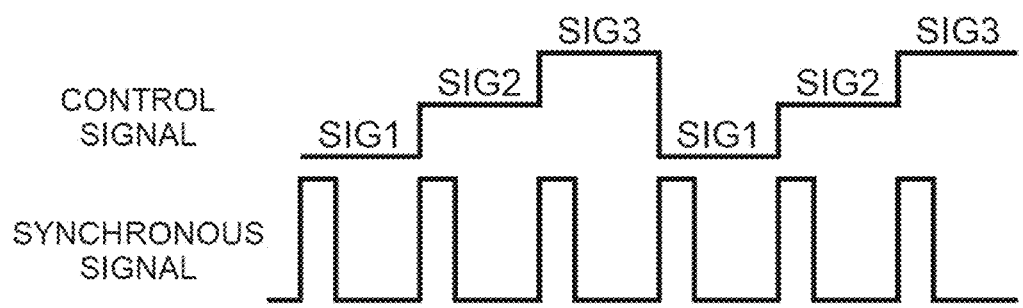

Fig.4
(A)
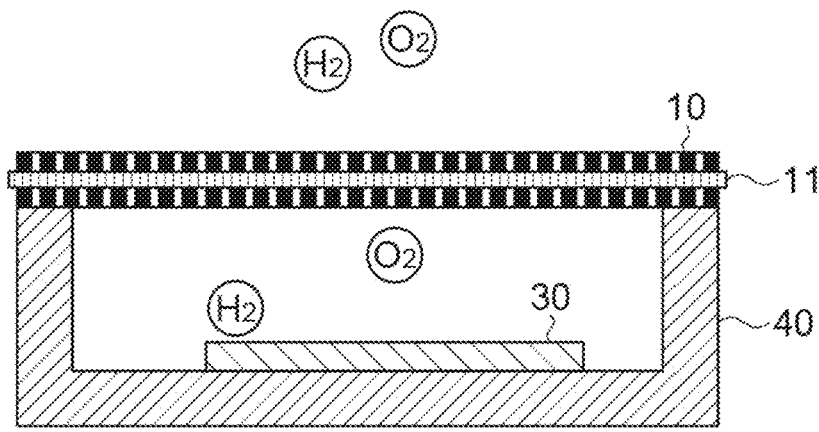
(B)
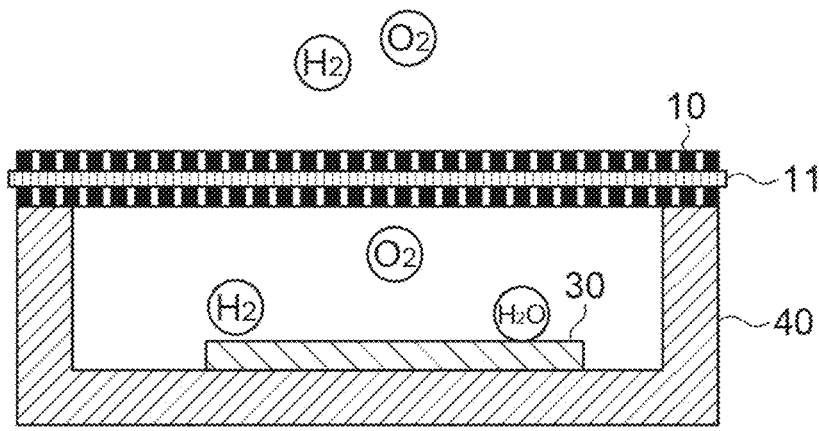
(C)
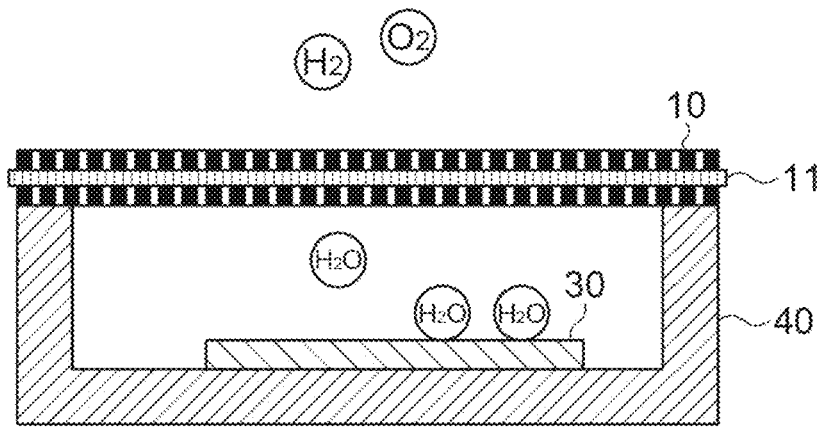

GAS MEASUREMENT DEVICE AND GAS MEASUREMENT METHOD

TECHNICAL FIELD

The present disclosure relates to a gas measurement device and a gas measurement method.

BACKGROUND ART

Patent Document 1 discloses a gas sensor. The gas sensor includes an electrode formed of a Pt porous body. When a voltage is applied to the electrode, oxygen held in the pores of the Pt porous body is dissociated. The gas sensor detects a current value generated by dissociated oxygen to detect an oxygen concentration.

CITATION LIST

Patent Document

Patent Document 1: Japanese Unexamined Patent Publication No. H11-281612

The gas to be measured may include a plurality of types of gases. In such a case, since the gas sensor described in Patent Document 1 is used exclusively for a specific gas, cannot measure a plurality of types of gases. The present disclosure provides a gas measurement device and a gas measurement method capable of detecting a plurality of types of gases.

Solution to Problem

A gas measurement device according to one aspect of the present disclosure includes a catalyst member and a gas sensor. The catalyst member is connected to a power source for applying voltage or current, and, performs a reaction of a first gas and a second gas contained in a mixed gas contacted with the catalyst member to generate a third gas, and exhibits a catalytic action in which the reaction changes in response to temperature. The gas sensor detects gas molecules contacted with the catalyst member.

In this gas measurement device, the temperature of the catalyst member changes when voltage or current is applied to the catalyst member. The reaction of the gas changes according to the temperature of the catalyst member. Therefore, the gas measurement device can change the type of gas molecules detected by the gas sensor by changing the temperature of the catalyst member. Therefore, the gas measurement device can detect a plurality of types of gases as compared with a gas measurement device specialized for a specific gas.

A gas measurement device according to another aspect of the present disclosure includes a catalyst member, a temperature adjustment mechanism, and a gas sensor. The catalyst member performs a reaction of a first gas and a second gas contained in a mixed gas contacted with the catalyst member to generate a third gas, and exhibits a catalytic action in which the reaction changes in response to temperature. The temperature adjustment mechanism is connected to a power source for applying voltage or current, and adjusts the temperature of the catalyst member. The gas sensor detects gas molecules contacted with the catalyst member. In this gas measurement device, the temperature of the catalyst member is changed by the temperature adjusting mechanism. The reaction of the gas changes according to the temperature of the catalyst member. Therefore, the gas measurement device can change the type of gas molecules detected by the gas sensor by changing the temperature of the catalyst member. Therefore, the gas measurement device can detect a plurality of types of gases as compared with a gas measurement device specialized for a specific gas.

In one embodiment, the gas measurement device may further include a plurality of gas sensors including the gas sensor. The plurality of gas sensors includes another gas sensor configured to detect a gas molecule different from a gas species of the gas molecule detected by the gas sensor. In this case, the gas measurement device can measure a plurality of types of gases.

In one embodiment, the gas measurement device may further include a signal generation unit, a control unit, an acquirement unit, and an output unit. The signal generation unit outputs a synchronous signal for determining timing. The control unit controls the power source based on the control signal for determining the temperature of the catalyst member and the synchronous signal so that the temperature of the catalyst member becomes the temperature determined by the control signal at the timing determined by the synchronous signal. The acquirement unit acquires a detection value of the gas sensor at a timing determined by the synchronous signal. The output unit outputs the detection value and the control signal in association with each other. In this case, the gas measurement device can output the detection value and the synchronous signal in association with each other.

In one embodiment, the gas measurement device may further include a determination unit. The determination unit determines the gas species based on a pre-acquired relationship, the detection value, and the control signal. The pre-acquired relationship is a relationship between the gas species, the detection value, and the control signal. In this case, the gas measurement device can determine the gas species of the mixed gas including the first gas and the second gas which react by the catalyst member to generate the third gas.

A gas measurement method according to another aspect of the present disclosure includes the following steps (1) to (4).
  (1) controlling the temperature of the catalyst member, and causing a first gas and a second gas contained in a mixed gas to react by a catalytic action of the catalyst member to generate a third gas. The generation of the third gas is based on a control signal for determining temperature of a catalyst member and a synchronous signal for determining a timing. The temperature of the catalyst member is determined by the control signal at the timing determined by the synchronous signal.
  (2) detecting, by a gas sensor, gas contacted with the catalyst member.
  (3) acquiring a detection value of the gas sensor at a timing determined by the synchronous signal.
  (4) determining the gas species based on a pre-acquired relationship, the acquired detection value, and the control signal, wherein the pre-acquired relationship is a relationship between the gas species and the detection value, the acquired detection value, and the control signal.

According to this gas measurement method, a plurality of types of gases can be detected.

Advantageous Effects of Invention

According to the gas measurement device and the gas measurement method of the present disclosure, a plurality of types of gases can be detected.

(A) of FIG. 2 is a block diagram illustrating an example of the gas measurement device according to the embodiment. (B) of FIG. 2 is an example of the control signal and the synchronous signal.

Figure 3:
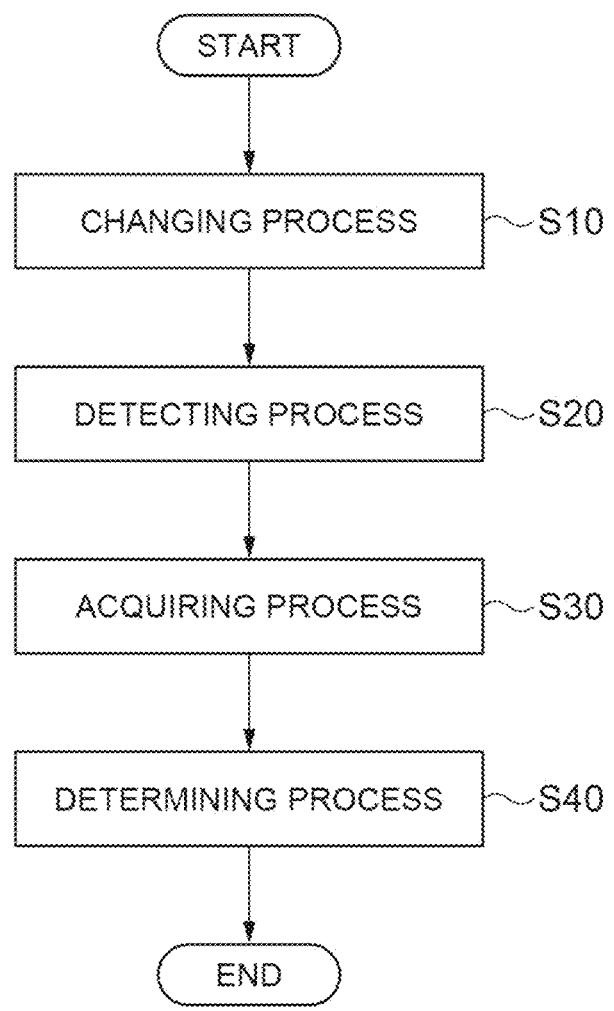

FIG. 3 is a flowchart illustrating an example of a gas measurement method according to an embodiment.

FIG. 4 is a schematic diagram illustrating the reaction of gas molecules according to the temperature of a catalyst member.

Figure 5:
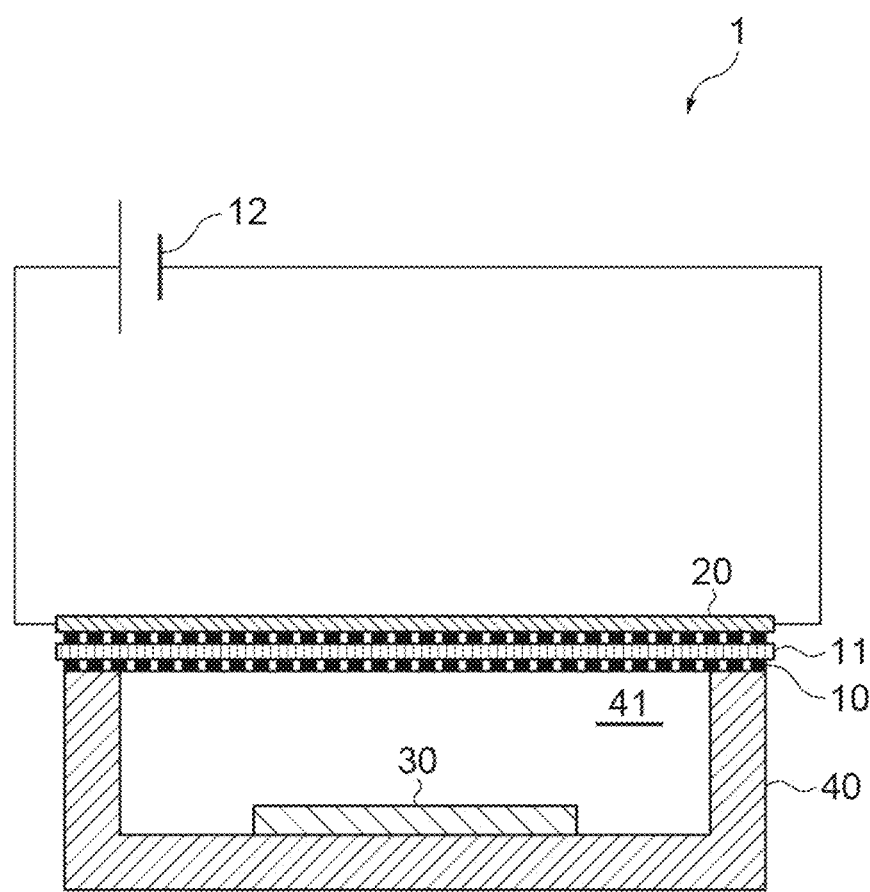

FIG. 5 is a cross-sectional view showing a modification of the gas measurement device according to the embodiment.

DESCRIPTION OF EMBODIMENTS

An embodiment of the present disclosure is described below with reference to the drawings. In the description below, the same or equivalent elements are denoted by the same reference characters, and overlapping description is not repeated. Dimension ratios of the drawings do not necessarily match with those described. Terms "up", "down", "left", and "right" are based on the illustrated states and are for convenience.

Figure 1:
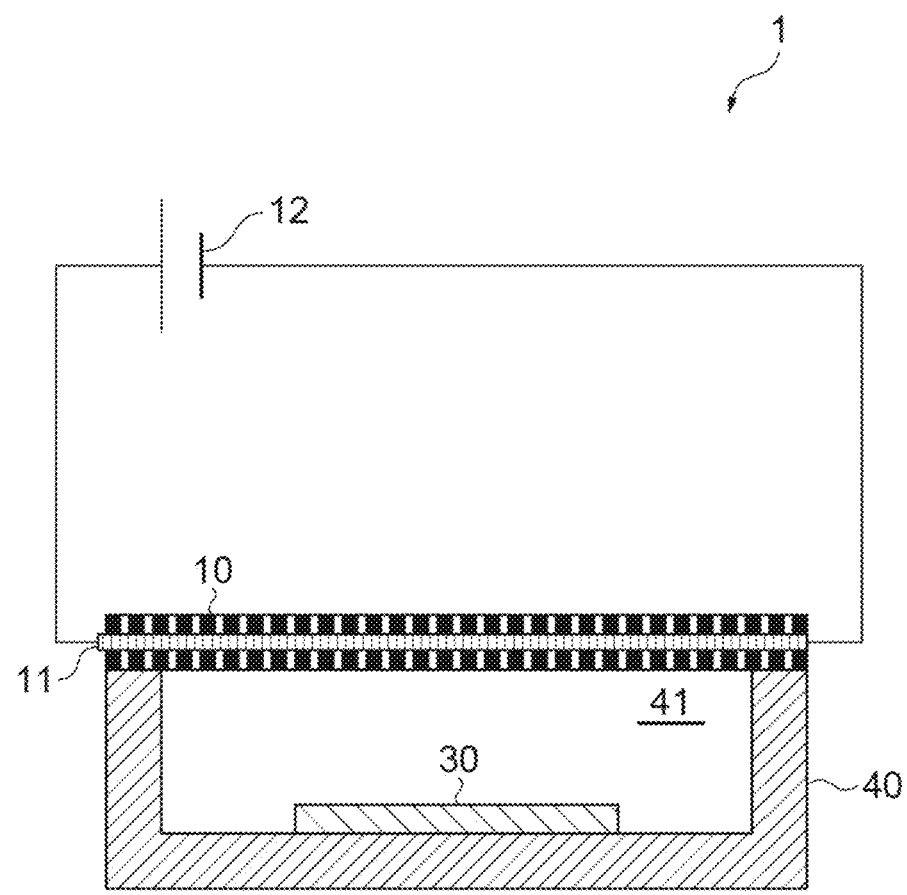
FIG. 1 is a cross-sectional view illustrating an example of a gas measurement device according to an embodiment.

[Configuration of Gas Measurement Device] FIG. 1 is a cross-sectional view illustrating an example of a gas measurement device according to an embodiment. A gas measurement device 1 shown in FIG. 1 is a device for measuring gas components. The gas measurement device 1 may be provided as an electric circuit component. As an example, the gas measurement device 1 is a micro electro mechanical systems (MEMS) device. The gas measurement device 1 includes a filter 10, a catalyst member 11, a base member 40, and a gas sensor 30.

The base member 40 defines a space therein. The base member 40 is formed of a gas-impermeable material. The base member 40 is open at its upper portion and has an opening communicating with the space. The filter 10 is disposed so as to close the opening in the upper portion of the base member 40. The filter 10 is a substantially plate-shaped member and is formed of a material that allows gas to pass therethrough. The filter 10 and the base member 40 are joined so that there is no gap through which gas passes. Thus, the filter 10 and the base member 40 define a gas chamber 41.

The filter 10 is provided with a catalyst member 11. The catalyst member 11 is an electric conductor and generates heat by energization. The catalyst member 11 is made of a metal catalyst such as platinum (Pt), titanium (Ti), or iridium (Ir), for example. The catalyst member 11 is connected to a power source 12 for applying voltage or current, and generates heat by voltage application or current application. When the gas measurement device 1 includes a plurality of catalyst members 11, the plurality of catalyst members 11 are disposed so as to be spaced apart from each other. Gas can pass between each of the plurality of catalyst members 11. The heated catalyst member 11 performs a catalytic action of reacting the first gas and the second gas contained in the mixed gas to generate the third gas. The catalyst member 11 is disposed so as to cover the substantially plate-shaped filter 10 in an in-plane direction. As an example, beam-shaped catalyst members 11 are arranged at predetermined intervals so as to cover the filter 10.

The gas sensor 30 is provided in the gas chamber 41. As an example, the gas sensor 30 is provided on the downstream of the catalyst member 11, that is, on the passing side where the gas has contacted with the catalyst member 11 and has passed through the vicinity of the catalyst member 11. The gas sensor 30 detects at least one of the first gas, the second gas, and the third gas generated by reaction. The gas sensor 30 is, for example, a gas sensor using a semiconductor. In this case, the gas sensor 30 outputs gas molecules in contact with the surface of the gas sensor 30 as an electric signal.

[Control Circuit of Gas Measurement Device] (A) of FIG. 2 is a block diagram illustrating an example of the gas measurement device 1A according to an embodiment. The gas measurement device 1A includes a measuring unit 2 (an example of a gas measurement device) and a circuit unit 3. The circuit unit 3 includes a signal generation unit 50, a control unit 60, an acquirement unit 70, an output unit 80, and a determination unit 90. The circuit unit 3 may be formed of, for example, an electric circuit. The circuit unit 3 may be configured by, for example, a general-purpose computer including an arithmetic device such as a central processing unit (CPU), a storage device such as a read only memory (ROM), a random access memory (RAM), and a hard disk drive (HDD), and a communication device.

The signal generation unit 50 outputs a control signal and a synchronous signal to the control unit 60 and the acquirement unit 70. The control signal is a signal for determining the temperature of the catalyst member 11. The synchronous signal is a signal that determines the timing between the control unit and the acquirement unit. The control unit 60 controls the power source 12 so as to apply voltage or current for controlling the temperature of the catalyst member 11 to the catalyst member 11 based on the control signal and the synchronous signal. (B) of FIG. 2 is an example of the control signal and the synchronous signal. In (B) of FIG. 2, the control signal is a signal corresponding to three kinds of temperatures of SIG1, SIG2, and SIG3. The synchronous signal is a rectangular wave based on an oscillator such as a crystal oscillator. The control unit 60 controls the temperature of the catalyst member 11 so as to be the temperature indicated by the control signal. The acquirement unit 70 acquires a detection value based on the synchronous signal.

When the rectangular wave of the synchronous signal is received a predetermined number of times, the control unit 60 outputs a control signal having a waveform corresponding to the temperature of the catalyst member 11. As an example, the control signal that changes in three stages in (B) of FIG. 2 controls the temperature of the catalyst member 11 in three stages. The temperature of the catalyst member 11 may be continuously controlled. In this case, the control signal indicates a triangular wave or a sine wave.

The acquirement unit 70 acquires the detection value when the rectangular wave of the synchronous signal is received a predetermined number of times. Therefore, the acquirement unit 70 can acquire the detection value corresponding to the change in the temperature of the catalyst member 11 caused by the control signal. The predetermined number of times of receiving the rectangular wave when the acquirement unit 70 acquires the detection value may be equal to or greater than the number of times of receiving the rectangular wave when the control unit 60 outputs the control signal. By making the timing at which the acquirement unit 70 acquires the detection value later than the timing at which the control unit 60 outputs the control signal, the acquirement unit 70 can acquire the detection value when a large number of gas molecules come into contact with the catalyst member 11 after the temperature of the catalyst member 11 has changed.

The output unit 80 outputs the control signal and the detection value acquired from the acquirement unit 70 in association with each other.

The determination unit 90 determines the gas species based on the pre-acquired relationship, the detection value and the control signal output by the output unit 80. The pre-acquired relationship is a relationship between the gas species, the detection value, and the control signal. The combination of the gas species, the detection value, and the control signal is acquired in advance and stored as, for example, a gas characteristic table. The determination unit 90 determines the gas species with reference to the gas characteristic table based on the combination output by the output unit 80.

[Operation of Gas Measurement device] FIG. 3 is a flowchart illustrating an example of the gas measurement method according to an embodiment. The steps of the flow chart shown in FIG. 3 illustrate the operation of the gas measurement device 1A. FIG. 4 is a schematic view illustrating the reaction of gas molecules according to the temperature of the catalyst member. As an example, the gas to be detected is a mixed gas containing hydrogen ($H_2$) and oxygen ($O_2$). The gas measurement device 1A includes a gas sensor 30 capable of detecting hydrogen ($H_2$).

As shown in FIG. 3, first, the temperature of the catalyst member 11 is changed by the control unit 60 that operates based on the control signal and the synchronous signal (step S10). (A) of FIG. 4 shows the reaction of gas molecules in contact with the catalyst member 11 when the control signal is SIG1. As an example, when the control signal is SIG1, the control unit 60 controls the power source 12 so as not to apply voltage or current to the catalyst member 11. Therefore, the catalyst member 11 does not generate heat. When the control signal is SIG1, then hydrogen ($H_2$) does not react with oxygen ($O_2$). The gas sensor 30 mainly detects hydrogen ($H_2$) (step S20).

(B) of FIG. 4 shows the reaction of gas molecules in contact with the catalyst member 11 when the control signal is SIG2. When the control signal is SIG2, the control unit 60 controls the power source 12 to apply voltage or current to the catalyst member 11. The catalyst member 11 that has generated heat by energization causes a reaction between hydrogen ($H_2$) and oxygen ($O_2$). Therefore, when the control signal is SIG2, water ($H_2O$) is generated by a reaction between hydrogen ($H_2$) and oxygen ($O_2$). In this case, water ($H_2O$) is produced by the reaction of part of hydrogen ($H_2$) and part of oxygen ($O_2$) that have contacted the catalyst member 11. Therefore, the gas sensor 30 detects hydrogen ($H_2$) after water ($H_2O$) is generated (step S20).

(C) of FIG. 4 shows the reaction of gas molecules in contact with the catalyst member 11 when the control signal is SIG3. When the control signal is SIG3, the control unit 60 controls the power source 12 so as to apply larger voltage or current to the catalyst member 11 than when the control signal is SIG2. The catalyst member 11 that has generated heat by energization causes a reaction between hydrogen ($H_2$) and oxygen ($O_2$). In this case, all of the hydrogen ($H_2$) and oxygen ($O_2$) in contact with the catalyst member 11 react to produce water ($H_2O$). The gas sensor 30 detects the absence of hydrogen ($H_2$) (step S20).

Next, the acquirement unit 70 acquires the measurement value output by the gas sensor 30 based on the synchronous signal (step S30).

The determination unit 90 determines the gas species based on the gas characteristic table, the measurement value acquired by the acquirement unit 70, and the control signal (step S40). From the previously acquired relationship between the temperature of the catalyst member 11 indicated by the control signal and the measured value, it is determined that the mixed gas contains hydrogen ($H_2$) and oxygen ($O_2$).

[Summary of Embodiment] In the gas measurement device 1, the temperature of the catalyst member 11 changes when voltage or current is applied to the catalyst member 11. The reaction of the gas changes according to the temperature of the catalyst member 11. Therefore, the gas measurement device 1 can change the type of gas molecules detected by the gas sensor 30 by changing the temperature of the catalyst member 11. Therefore, the gas measurement device 1 can detect a plurality of types of gases as compared with a gas measurement device specialized for a specific gas.

The gas measurement device 1A includes a signal generation unit 50 for outputting a synchronous signal, a control unit 60 for controlling the temperature of the catalyst member 11 based on a control signal for determining the temperature of the catalyst member 11 and the synchronous signal, an acquirement unit 70 for acquiring the detection value of the gas sensor 30 based on the synchronous signal, and an output unit 80 for outputting the detection value and the control signal in association with each other. In this case, the gas measurement device 1A can output the detection value and the synchronous signal in association with each other.

A gas measurement device 1A and a gas measurement method include a determination unit 90 for determining a gas species based on a pre-acquired relationship, the detection value and the control signal output by an output unit 80. The pre-acquired relationship is a relationship between the gas species, a detection value, and a control signal. In this case, the gas measurement device 1A and the gas measurement method can determine the gas species of the mixed gas including the first gas and the second gas that react by the catalyst member 11 to generate the third gas.

[Modification] While various exemplary embodiments have been described above, various omissions, substitutions and changes may be made without being limited to the exemplary embodiments described above.

FIG. 5 is a cross-sectional view showing a modification of the gas measurement device according to the embodiment. The gas measurement device 1B includes a catalyst member 11 that reacts the first gas and the second gas contained in a mixed gas to generate the third gas, a heating unit 20 (an example of a temperature adjustment mechanism) that is connected to a power source 12 that applies voltage or current and changes the temperature of the catalyst member 11, and a gas sensor 30 that detects at least one of the first gas, the second gas, and the third gas generated by reaction.

The heat generator 20 is an electrical conductor and generates heat when energized. For example, the heat generator 20 is a nichrome wire. The heat generator 20 reacts the first gas and the second gas contained in a mixed gas by heating the catalyst member 11 to generate the third gas. In the gas measurement device 1B, the catalyst member 11 may not generate heat. The catalyst member 11 may be supported by an insulator. In addition, the gas measurement device 1B may include a cooling unit (an example of a temperature adjustment mechanism) instead of the heat generator 20.

The temperature of the catalyst member 11 is changed by the heat generator 20. By changing the temperature of the catalyst member 11, the gas measurement device 1B can change the gas species detected by the gas sensor 30 and measure a plurality of gas species. Therefore, the gas measurement device 1B can detect a plurality of types of gases as compared with a gas measurement device specialized for a specific gas.

The gas measurement device 1 may include a plurality of gas sensors including the gas sensor 30. In a case where the first gas sensor 31 (an example of the gas sensor 30) and the second gas sensor 32 (an example of another gas sensor) are provided, the second gas sensor 32 may be configured to be capable of mainly detecting gas molecules of a type different from gas molecules detected by the first gas sensor 31. In this case, the gas measurement device can measure a plurality of types of gases.

The filter 10 and the gas sensor 30 may be formed separately and then assembled together. The filter 10 and the gas sensor 30 may be integrally manufactured.

The signal generation unit 50 may be integrated with the control unit 60. The acquirement unit 70 may be integrated with the output unit 80. The output unit 80 may be integrated with the determination unit 90.

The gas measurement device 1 may be configured not to include the base member 40 and the gas chamber 41. In this case, the gas measurement device 1 is configured such that the catalyst member 11 of the filter 10 is in close contact with the gas sensor 30. The gas measurement device 1 may include M types of gas sensors (M is an integer of 2 or more). When M is 3 or more, the M types of gas sensors may include the same type of sensor. The temperature of the catalyst member 11 may be controlled in N stages (N is an integer of 2 or more). In this case, the gas measurement device 1 can measure the gas in a combination of M×N types at maximum.

The gas measurement device 1A may be configured not to include the determination unit 90. In this case, the output unit 80 of the gas measurement device 1A outputs the measured value and the control signal to the outside. The gas measurement device 1A may acquire the relationship between the measured value and the control signal in advance by simulation. In this case, the temperature of the catalyst member 11 and the speed at which the third gas is generated are obtained by calculation. The relationship between the measured value and the control signal may be calibrated with a known gas. In this case, the relationship between the control signal and the temperature of the catalyst member 11 and the output characteristic of the gas sensor 30 are calibrated based on the known gas in which the gas species and the generated third gas are specified.

REFERENCE SIGNS LIST

1, 1A, 1B . . . gas measurement device, 2 . . . measuring unit, 3 . . . circuit unit, 10 . . . filter, 11 . . . catalyst member, 20 . . . heat generator, 30 . . . gas sensor, 40 . . . base member, 41 . . . gas chamber, 50 . . . signal generation unit, 60 . . . control unit, 70 . . . acquirement unit, 80 . . . output unit, 90 . . . determining unit.

The invention claimed is:

1. A gas measurement device comprising:
a base member having an opening at its upper portion and formed of a gas-impermeable material;
a filter disposed so as to close the opening and formed of a gas-permeable material;
a gas chamber defined by the base member and the filter;
a gas sensor disposed in the gas chamber;
a catalyst member connected to a power source applying voltage or current, performing a reaction of a first gas and a second gas contained in a mixed gas contacted with the catalyst member to generate a third gas, and exhibiting a catalytic action in which the reaction changes in response to temperature;
a signal generation unit configured to output a synchronous signal for determining timing;
a control unit configured to control the power source based on a control signal for determining temperature of the catalyst member and the synchronous signal so that the temperature of the catalyst member becomes a temperature determined by the control signal at the timing determined by the synchronous signal;
an acquirement unit configured to acquire a detection value of the gas sensor at the timing determined by the synchronous signal; and
an output unit configured to output the detection value and the control signal in association with each other, wherein
the filter has the catalyst, and
the gas sensor is configured to detect gas molecules contacted with the catalyst member, and
the control unit is configured to output the control signal having a waveform corresponding to the temperature of the catalyst member when the rectangular wave of the synchronous signal is received a predetermined first number of times, and
the acquirement unit is configured to acquire the detection value when the rectangular wave of the synchronous signal is received a predetermined second number of times.

2. The gas measurement device according to claim 1, further comprising a plurality of gas sensors including the gas sensor,
wherein the plurality of gas sensors includes another gas sensor configured to detect a gas molecule different from a gas species of the gas molecule detected by the gas sensor.

3. The gas measurement device according to claim 1, further comprising a determination unit configured to determine the gas species based on a pre-acquired relationship, the detection value, and the control signal,
wherein the pre-acquired relationship is a relationship between the gas species, the detection value, and the control signal.

4. The gas measurement device according to claim 1, wherein the first gas is hydrogen, and the second gas is oxygen, and the third gas is water, and the gas sensor is configured to detect hydrogen contained in the mixed gas after contacting with the catalyst member.

5. The gas measurement device according to claim 4, further comprising a plurality of gas sensors including the gas sensor,
wherein the plurality of gas sensors includes another gas sensor configured to detect a gas molecule different from hydrogen detected by the gas sensor.

6. The gas measurement device according to claim 1, wherein the predetermined second number of times is larger than the predetermined first number of times.

7. A gas measurement device comprising:
a base member having an opening at its upper portion and formed of a gas-impermeable material;
a filter disposed so as to close the opening and formed of a gas-permeable material;
a gas chamber defined by the base member and the filter;
a gas sensor disposed in the gas chamber;
a catalyst member performing a reaction of a first gas and a second gas contained in a mixed gas contacted with the catalyst member to generate a third gas, and exhibiting a catalytic action in which the reaction changes in response to temperature;

a temperature adjustment mechanism connected to a power source applying voltage or current and configured to adjust temperature of the catalyst member;

a signal generation unit configured to output a synchronous signal for determining timing;

a control unit configured to control the power source based on a control signal for determining temperature of the catalyst member and the synchronous signal so that the temperature of the catalyst member becomes a temperature determined by the control signal at the timing determined by the synchronous signal;

an acquirement unit configured to acquire a detection value of the gas sensor at the timing determined by the synchronous signal; and an output unit configured to output the detection value and the control signal in association with each other, wherein the filter has the catalyst, and the gas sensor is configured to detect gas molecules contacted with the catalyst member, and the control unit is configured to output the control signal having a waveform corresponding to the temperature of the catalyst member when the rectangular wave of the synchronous signal is received a predetermined first number of times, and the acquirement unit is configured to acquire the detection value when the rectangular wave of the synchronous signal is received a predetermined second number of times.

8. The gas measurement device according to claim 7, further comprising a plurality of gas sensors including the gas sensor, wherein the plurality of gas sensors includes another gas sensor configured to detect a gas molecule different from a gas species of the gas molecule detected by the gas sensor.

9. The gas measurement device according to claim 7, further comprising a determination unit configured to determine the gas species based on a pre-acquired relationship, the detection value, and the control signal, wherein the pre-acquired relationship is a relationship between the gas species, the detection value, and the control signal.

10. The gas measurement device according to claim 7, wherein the first gas is hydrogen, and the second gas is oxygen, and the third gas is water, and the gas sensor is configured to detect hydrogen contained in the mixed gas after contacting with the catalyst member.

11. The gas measurement device according to claim 10, further comprising a plurality of gas sensors including the gas sensor, wherein the plurality of gas sensors includes another gas sensor configured to detect a gas molecule different from hydrogen detected by the gas sensor.

12. The gas measurement device according to claim 7, wherein the predetermined second number of times is larger than the predetermined first number of times.

13. A gas measurement method comprising:

controlling, based on a control signal for determining temperature of a catalyst member and a synchronous signal for determining a timing, the temperature of the catalyst member so as to be the temperature determined by the control signal at the timing determined by the synchronous signal, and causing a first gas and a second gas contained in a mixed gas to react by a catalytic action of the catalyst member to generate a third gas;

detecting, by a gas sensor, gas contacted with the catalyst member;

acquiring a detection value of the gas sensor at a timing determined by the synchronous signal;

determining the gas species based on a pre-acquired relationship, the acquired detection value, and the control signal, wherein the pre-acquired relationship is a relationship between the gas species and the detection value, the acquired detection value, and the control signal;

outputting the control signal having a waveform corresponding to the temperature of the catalyst member when the rectangular wave of the synchronous signal is received a predetermined first number of times; and acquiring the detection value when the rectangular wave of the synchronous signal is received a predetermined second number of times, wherein the gas sensor is provided in a gas chamber, the gas chamber is provided on the downstream of the catalyst member, the gas chamber is defined by a base member having an opening at its upper portion and formed of a gas-impermeable material and a filter disposed so as to close the opening and formed of a gas-permeable material, and the filter has the catalyst.

14. The gas measurement method according to claim 13, wherein the first gas is hydrogen, and the second gas is oxygen, and the third gas is water, and the gas sensor is configured to detect hydrogen contained in the mixed gas after contacting with the catalyst member.

15. The gas measurement method according to claim 14, further comprising a plurality of gas sensors including the gas sensor, wherein the plurality of gas sensors includes another gas sensor configured to detect a gas molecule different from hydrogen detected by the gas sensor.

16. The gas measurement method according to claim 13, wherein the predetermined second number of times is larger than the predetermined first number of times.

* * * * *